United States Patent

Schweitzer et al.

[11] Patent Number: 5,984,474
[45] Date of Patent: Nov. 16, 1999

[54] ARRANGEMENT AND METHOD FOR TIME-RESOLVED MEASUREMENT ACCORDING TO THE SCANNER PRINCIPLE

[75] Inventors: Dietrich Schweitzer, Neustadt/Orla; Martin Hammer, Jena; Wolfgang Triebel, Jena; Karl-Heinz Donnerhacke, Jena; Theo Lasser, Oberkochen, all of Germany

[73] Assignee: Carl Zeiss Jena GmbH and Institut Fuer Physikalische Hochternologie, Jena, Germany

[21] Appl. No.: 09/085,751

[22] Filed: May 28, 1998

[30] Foreign Application Priority Data

May 30, 1997 [DE] Germany ................. 197 22 790

[51] Int. Cl.⁶ ..................................... A61B 3/10
[52] U.S. Cl. ......................................... 351/205
[58] Field of Search ................... 359/368, 389; 382/128; 351/205, 216, 220, 221, 246

[56] References Cited

U.S. PATENT DOCUMENTS 5,016,173  5/1991  Kenet et al. ................. 382/128
5,760,950  6/1998  Maly et al. .................. 359/368

*Primary Examiner*—George Manuel
*Attorney, Agent, or Firm*—McAulay Nissen Goldberg Kiel & Hand, LLP

[57] ABSTRACT

An arrangement for spatially resolved acquisition of an object which is illuminated by an illumination arrangement, wherein a relative movement is generated between the illumination arrangement and the object by moving the object and/or the illumination arrangement and, in addition to at least one confocally arranged detection element for confocal acquisition of the light coming from points on the object, there is provided at least one additional detection element for the acquisition of object light at least posterior in time to the confocal acquisition. For at least two-dimensionally spatially resolved measurement of time processes, especially of fluorescence decay times, preferably at the ocular fundus, using a scanning laser ophthalmoscope, the radiation receiver is at least a series of detectors which are arranged in such a way that there is a series of additional detector elements in addition to the confocal detector element at least subsequently in the scanning direction.

23 Claims, 5 Drawing Sheets

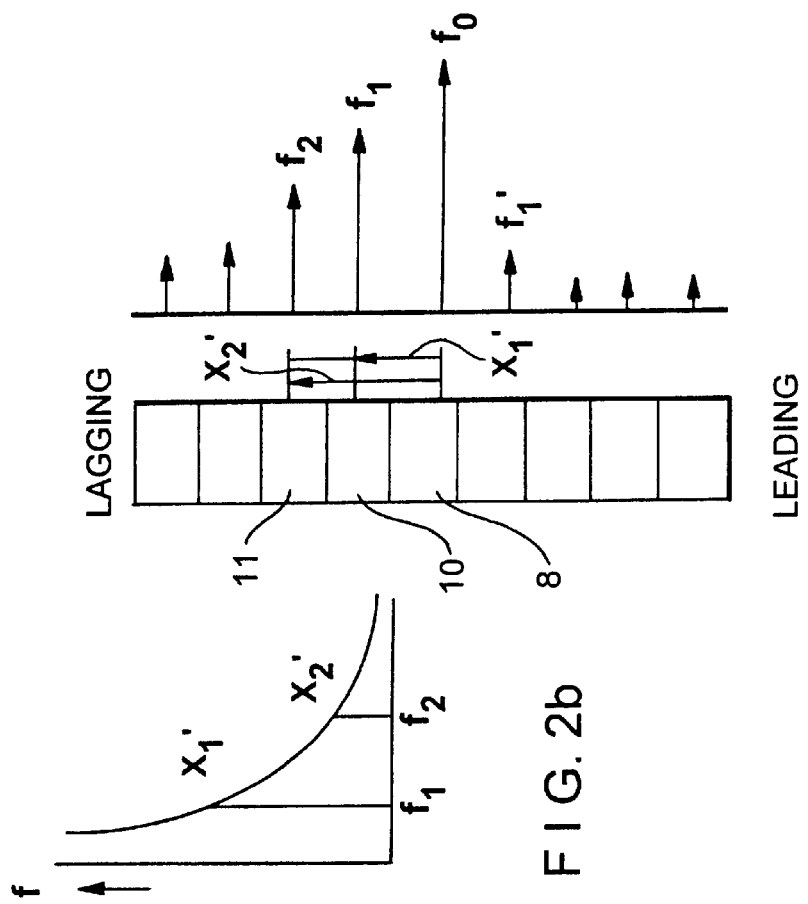
FIG. 2a
FIG. 2b
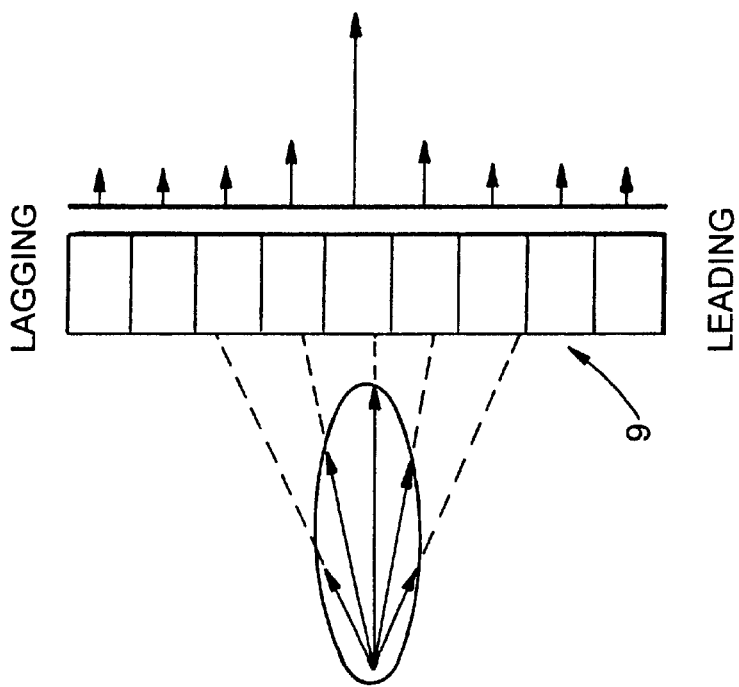
FIG. 2c

ARRANGEMENT AND METHOD FOR TIME-RESOLVED MEASUREMENT ACCORDING TO THE SCANNER PRINCIPLE

BACKGROUND OF THE INVENTION

Scanning laser ophthalmoscopes are used to examine the ocular fundus and have the following advantages over known retina cameras for photometric measurements:

the asymmetric division of the aperture diaphragm in the eye pupil to the advantage of the measurement aperture;

the high radiation intensity permissible for brief periods on a small examination location;

the basic possibility of measuring in the direction of the optical axis (scanning laser tomography).

Scanning laser ophthalmoscopes carrying out point-by-point scanning of the ocular fundus are known, wherein a detector records the light reflected from every point on the ocular fundus. An image of the ocular fundus is formed after synchronous assignment of the image points to a line and, further, of the lines to an image. This image can be a reflection image or —when a blocking filter is incorporated —a fluorescence image. The image obtained in this way can be stored digitally after analog-to-digital conversion of the pixel signals and is then available for further image processing.

An ophthalmoscope of this kind is described, for example, in WO 88/03396 and DE 3638226 A1. In these cases, a plurality of individual detectors which are preferably arranged in the shape of a circle sector are provided for the acquisition and detection of the surface intensity distribution of the reflected light from different planes and its polarization state.

DE 3818084 A1 likewise describes an ocular fundus camera with laser beam scanning in which a reflection image is obtained simultaneous with the florescence image for focussing the image of the ocular fundus during fluorescein angiography.

EP 307185 A2 is directed to a scanning device with a detector array and with an anamorphotic element for generating a stripe-shaped focussed image which is guided over the retina.

DE 3037983 C2 is not related to raster-type detection of the ocular fundus. An embodiment example relates to scanning by means of a diode array which extends in the scanning direction as a receiver. Only the point on the sample or specimen that is being illuminated at the moment is imaged on an available receiver. The behavior of the fluorescent radiation with respect to time can be adjusted by selecting determined diode groups and a delay time between the illumination of the point on the specimen and the detection of fluorescent radiation. The diodes are read out synchronous with the scanning frequency. For the individual points on the specimen, the type of scanning gives various possibilities for detecting values at all. There is a conflict between the relationship to scanning speed and scanning frequency on the one hand and the desired acquisition of time processes such as fluorescence which last longer than the time period of a scanning step on the other hand. In the microscope described in CZ 4966 DE, the relationship to scanning frequency is abandoned, but the arrangement is then no longer suitable for normal scanning image generation.

OBJECT AND SUMMARY OF THE INVENTION

The primary object of the invention is two-dimensional image acquisition and measurement of time processes, preferably at the human ocular fundus in vivo.

In accordance with the invention, an arrangement is provided for spatially resolved acquisition of an object which is illuminated by means of an illumination arrangement, wherein a relative movement is generated between the illumination arrangement and the object by moving the object and/or the illumination arrangement and, in addition to at least one confocally arranged detection element for confocal acquisition of the light coming from points on the object, there is provided at least one additional detection element for the acquisition of object light at least posterior in time to the confocal acquisition.

In particular, the invention can be used to measure decay times of fluorophores so as to make it possible to distinguish between different fluorophores with similar fluorescence spectra but with sharply divergent fluorescence intensities.

It is possible to derive information on the characteristics of the surrounding medium from changes in the decay time of known fluorophores (quenching). Examinations of the above type on the human eye in vivo make it possible in principle to diagnose metabolic function before a disease causes morphological changes which can then be detected in the reflected light. An advantage of the proposed invention consists in that a clinically conducted technique is used as a basis and a new quality of measurements is achieved in an economical manner by expanding this technique. A time-resolved measurement of the fluorescence of a specimen is carried out without using wavelength-selective elements by means of subtraction of signals from paired leading and lagging detectors, so that the influence of reflected light, scattered light, and static fluorescent light is eliminated.

The arrangement according to the invention is described further hereinafter with reference to the schematic drawings.

BRIEF DESCRIPTION OF THE DRAWINGS

In the drawings:

FIG. 2 is a schematic illustration of the superposition of time-dependent fluorescent light with reflected, scattered and static fluorescent light;

Figure 5C:
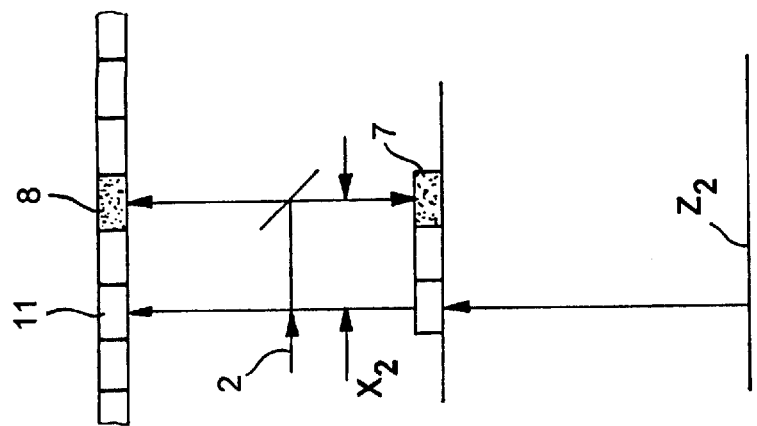
Figure 5B:
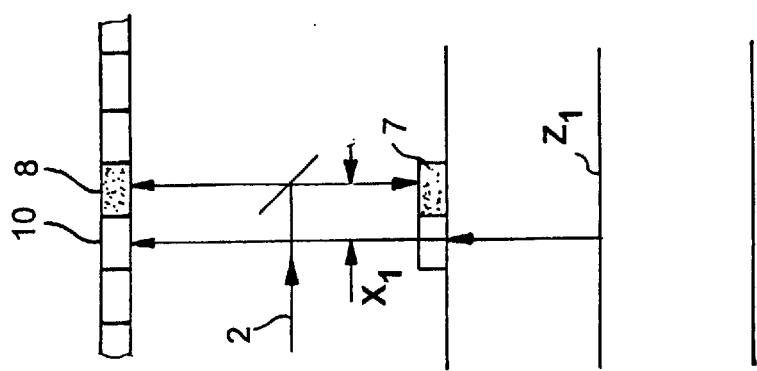
Figure 5A:
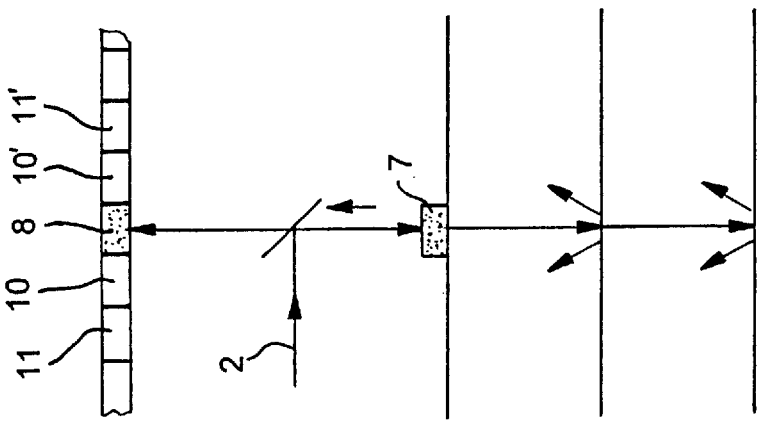

a) for short fluorescence lifetimes along the scanning direction in a line b) for longer fluorescence lifetimes along a column c) for fast scanning of the total image through parallel scanning of a line and scanning of the fluorescence signals in the columns of a matrix;

FIGS. 5a–c illustrate the retrieval of information from different tissue depths through measurement of different light travel times;

FIG. 5a illustrates the detection of the surface reflection light through confocal scanning;

FIG. 5b illustrates the detection of light from a middle intermediate "layer" and FIG. 5c illustrates the detection of light from a deeper intermediate layer.

DESCRIPTION OF THE PREFERRED EMBODIMENTS

Figure 1:
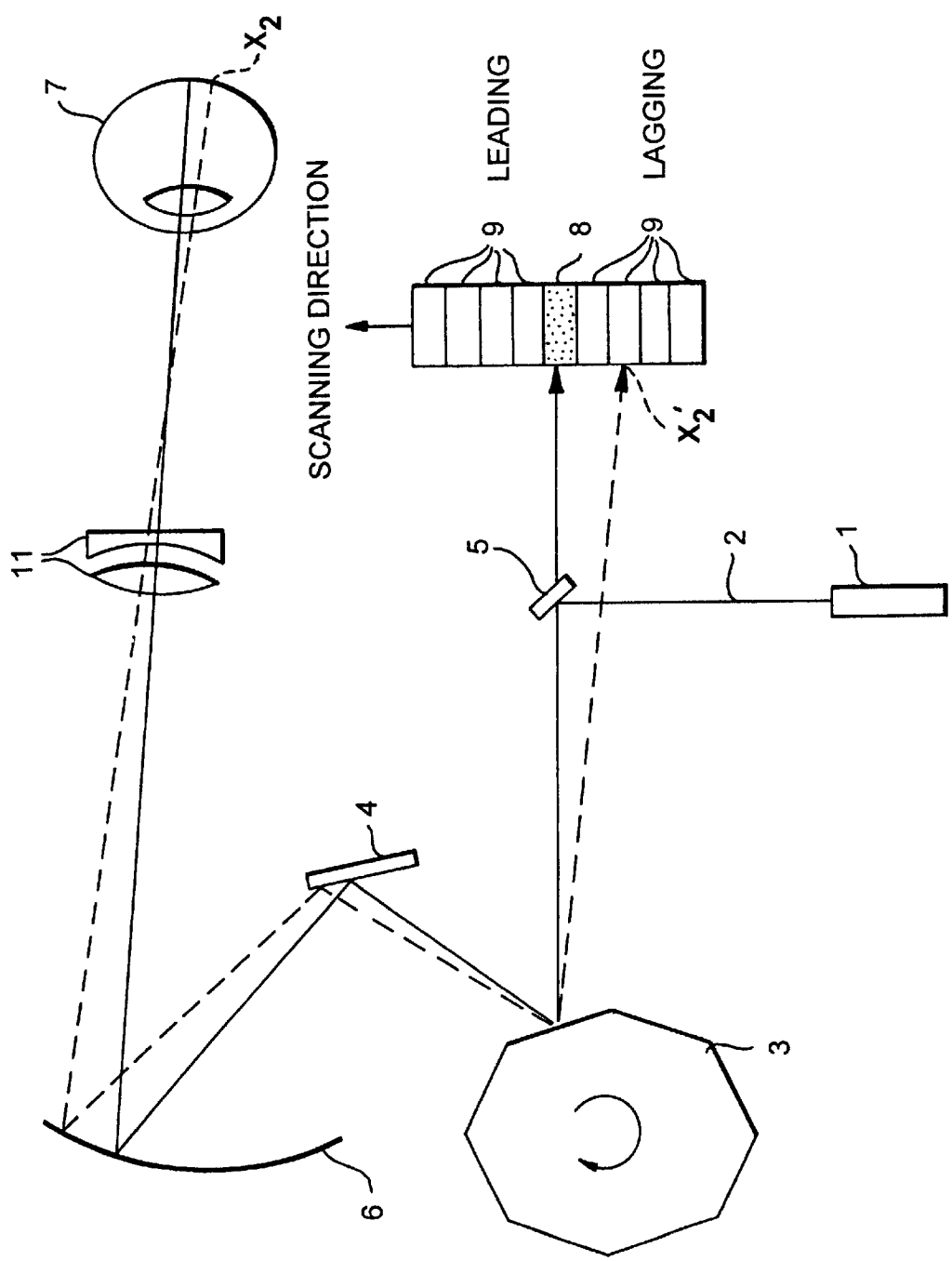
FIG. 1 is a schematic illustration of the arrangement for measuring time processes in the ocular fundus.

In FIG. 1, a laser 1 delivers a continuous or pulsed excitation beam 2 by way of a beam splitter 5. The excitation beam 2 is guided over a specimen 7, preferably the ocular fundus, after being deflected by a polygon scanner 3 for scanning in a line and by a galvanometer scanner 4 for the deflection of the lines in an image after imaging through the concave mirror 6 via correction optics 11 at a constant speed and briefly excites the specimen 7 to fluorescence, wherein the excitation can be effected by the radiation output acting during the sweep period or by a short light pulse during the sweep.

In confocal imaging, a reflected light and—after filtering—a static fluorescent light determined at the moment of impingement of the excitation beam 2 are measured from an illuminated point on the ocular fundus by an individual detector 8.

Figure 4A:
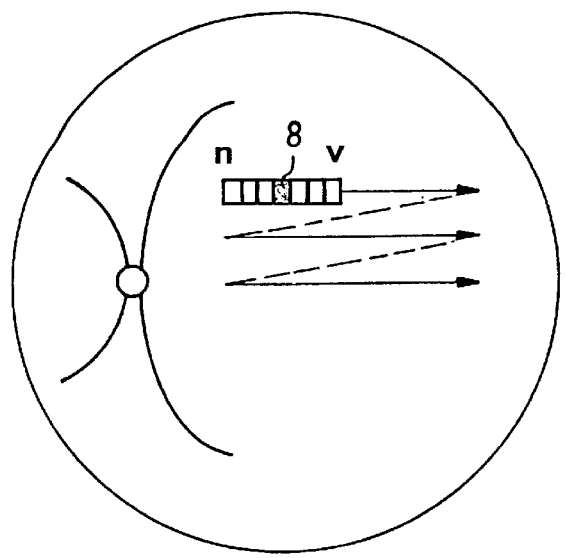
FIG. 4 shows different arrangements of detectors comprising a plurality of elements, where v=leading and n=lagging.

According to the invention, a multiple-detector arrangement 9 is arranged in addition to the confocally acting individual detector 8. This multiple-detector arrangement 8 is preferably a linear arrangement in which a sequence of detectors which are preferably identical is arranged on both sides of the confocal detector in a symmetric manner with respect to the confocal detector 8. This multiple-detector arrangement 9 is oriented along a line, preferably parallel to the scanning direction of the laser spot identified by an arrow (FIG. 4a). In this case, also, the detector 8 in a confocal arrangement records the reflected light and/or, after spectral filtering, the static fluorescent light of an excited location on the specimen 7.

When the fluorescent light has continued to radiate for a determined period of time without being excited simultaneously and the excitation beam has moved beyond the excited location of the specimen 7 by distance x1 within a time t1 due to the constant scanning speed, shown in FIG. 2a, the fluorescent light which still radiates from the excited location on the specimen 7 and which is imaged in the detector plane in a known manner by the scanning system no longer strikes the confocal detector 8, but rather strikes a detector 10 which is displaced by distance x1' relative to the confocal detector B.

The distance x1' required for the measurement process is given by the measured delayed scanning of the fluorescence decay time and the scanning speed.

When the excitation beam 2 has moved beyond the excited location of the specimen 7 by distance x2 during time t2, the fluorescent light which is still emitted from the excited location of the specimen 7 at time t2 strikes a detector 11 which is arranged at a distance x2' from the confocal detector 8.

In this case, the fluorescent light must pass through the scanning system in the opposite direction to that of the excitation beam.

As a result of the arrangement according to the invention, there is a transformation or conversion from the temporal region to the spatial region. The scanning time ti is given by the distance xi of the i-th detector from the confocal detector and by the scanning speed at which the specimen 7 is scanned.

In this way, the time-dependent fluorescent light of an excited location on the specimen 7 is measured in determined time intervals, so that its course can be calculated from the sample points or support points obtained by the measurement.

FIG. 2b shows, by way of example, the decay behavior of the fluorescence of a point on a specimen with two times t1, t2 corresponding to the acquisition by detectors 10, 11.

As a result of the described illumination of the ocular fundus by an excitation beam and the scanning of the reflected light and of the static fluorescent light, as well as of the time-dependent fluorescent light which, in a known manner, undergoes a descanning in the same deflection system as that for the excitation beam with the proposed multiple-detector arrangement, information about the decay time behavior of the fluorescence is available for every scanned image point. The excitation beam scans a two-dimensional object. The confocal detector delivers the reflection image or, after filtering, the image of the static fluorescence. Every other detector likewise generates a complete image.

In this way, after an object is scanned, there are, in addition to the reflection image or the image of the static fluorescence, n additional images which correspond to delay times t1 to tn. The time constants calculated from the measurements of the fluorescence intensity at defined scanning times are displayed pixelwise in two dimensions and thus serve to characterize different substances or different states.

When n detectors are used, a fluorescence decay curve is sensed proceeding from the excitation time point through n temporally equidistant support points. Different areas of the decay curve can be examined by means of displacing individual detectors or the entire detector arrangement in the image plane vertical to the radiating direction, parallel to the scanning direction of the object, and relative to the confocal pixel. Decay curves with different time constants can be measured by changing the detector distance or the scanning speed.

The scanning speed of the laser beam, by which the object to be examined is scanned along a line with the multiple-detector arrangement, and the smallest realizable detector distance determine the temporal spacing of the support points for the calculation of the smallest resolvable decay time constants of the fluorescent light. If the multiple-detector arrangement corresponding to FIG. 4b is arranged along a column vertical to the scanning direction, the time between the scanning of adjacent lines determines the smallest temporal distance between the support points for calculating the decay time constant.

Since the column scanning speed, for example, with X/Y-scanners, is substantially slower than the line scanning speed, substantially longer decay times can be measured by arranging the multiple-detectors in parallel columns than by arranging multiple-detectors in parallel lines.

Figure 4C:
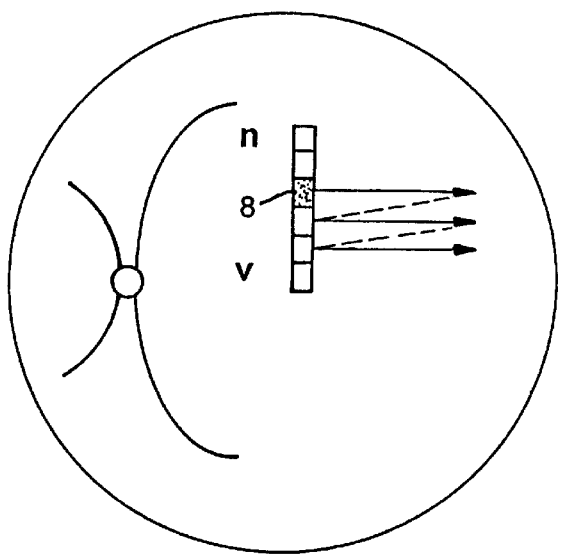
Figure 4B:
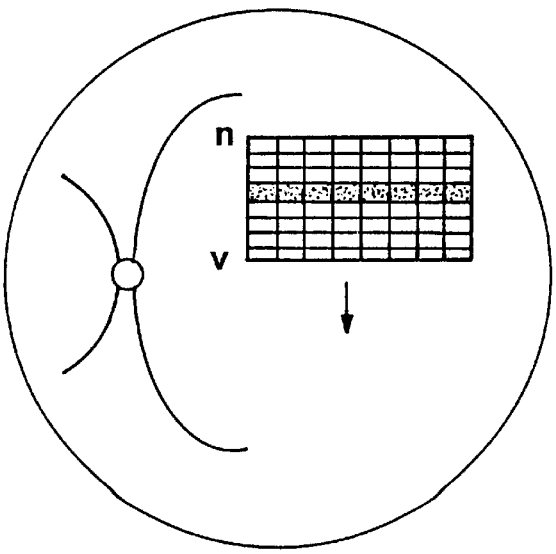

If the ocular fundus is scanned by a strip scanning method, for example, according to EP 307 185 A2, the multiple-detector arrangement according to FIG. 4c is a matrix which is moved in the direction of the arrow.

In this case, the confocal element is replaced by a confocal line. Every detector of the confocal line records the reflected light, the scattered light and the static fluorescent light in parallel.

The detector elements for measuring the fluorescent decay time are located in every column of the matrix, in each case adjacent to the confocal line.

The processing of the signals of the column elements is carried out in the same way as that already described with reference to FIG. 2.

A substantial advantage of this arrangement consists in the possibility of two-dimensional determination of the fluorescence decay behavior of short-lived fluorophores.

The synchronization of the scanning and measurement process is effected by means of a clock generator which is controlled by the polygon movement, that is, by the scanning movement in a line.

The quantity of image points in a line is counted and after reaching the required image points in a line, the line is switched ahead by control of a galvanometer scanner. When the required number of lines is reached within an image, the next image is formed. The reflection image as well as images of the ocular fundus which supply the fluorescent light according to defined times ti in two-dimensional rendering are detected by means of the arrangement according to the invention.

The fluorescence measured from the ocular fundus at different times after excitation is very small. Averaging is required in order to improve the signal-to-noise ratio. In the case of a stationary object, repeated recording and averaging of the images associated with every time delay ti is advantageous.

If the detectors are sufficiently sensitive, it is possible to measure the fluorescence decay time according to the principle of single photon counting. In this case, an accumulation of photons is effected with multiple scans of the object, these photons being recorded during the individual scans by every detector that is arranged at a distance corresponding to location xi from the confocal detector.

Eye movements during and between recordings must be taken into account under in vivo conditions at the human eye. Since there is a fixed correspondence or correlation between the confocal detector 8 and the elements of the multiple-detector arrangement 9, it is expedient and possible to carry out an active image position correction of the fluorescence images without distinct structural features within the fluorescence images based on anchor points in the high-contrast reflection image.

The coefficients of the transformation polynomials between a reference image and the other images which must be brought into coincidence with the reference image are determined for every measurement from the reflection image and applied for every pixel of a time-delayed image.

The invention can be used in a particularly advantageous manner for determination of two-dimensional fluorescence behavior of weakly fluorescent moving objects, since a high-contrast reference image is made available by means of the detection of the reflection image or the image of the static fluorescence, wherein an image position correction can also be carried out in the images associated with the delay times ti in accordance with the high-contrast reference image.

After the image position correction has been carried out, the images containing the fluorescence information at identical scanning time points are averaged so that a low-noise image can be calculated for every delay time ti in spite of the high-noise individual images in the case of a fixed time delay.

Averaging gives a set of images which are correlated in accordance with pixels and which represent the fluorescence intensity at different scanning time points.

The type of exponential drop-off and the associated time constants are determined from the disentanglement of the time-dependent course of the fluorescence at every pixel location by known methods of model matching. In this way, a two-dimensional distribution of fluorophores with different fluorescence decay times can be rendered, which makes it possible for the first time to distinguish between fluorophores with a similar fluorescence spectrum or widely divergent fluorescence intensity. In general, both reflected light and fluorescent light impinge on the detectors partially isotropically rather than in a directed manner. In order to eliminate the component of partially isotropically incident static fluorescent light and reflected light, an additional detector arrangement is arranged symmetric to the confocal detector and parallel to the scanning direction in addition to the detector arrangement which lags relative to the movement direction of the scanning beam, wherein this additional detector arrangement is arranged in an identical manner but measures only the partially isotropically incident static fluorescent light, the diffuse reflected light and the scattered light.

FIG. 2c shows schematically that in the event that the illuminated specimen does not exhibit any dynamic fluorescence behavior, equal proportions of reflected light and scattered light and static fluorescent light strike the leading and lagging detectors symmetrically. Since these proportions are superimposed on the dynamic fluorescence signal which is recorded only by the lagging detectors, the interfering influence of these components can be eliminated by paired substraction of signals from the symmetrically arranged leading and lagging detectors.

Due to the fact that the detector arrangements leading and lagging with respect to the movement direction of the excitation beam are constructed symmetrically, each leading detector $Di_{lead}$ measures the same partially isotropically incident static fluorescent light and the reflected light like every lagging detector $Di_{lag}$.

order to determine the time-dependent fluorescent light $F_{time}$ from the total light $Li_{lag}$ of the lagging detector $Di_{lag}$, the value $Li_{lead}$ is subtracted from $L_{i,lag}=L_{i,lead}+F_{time}$.

Surprisingly, through the use of a symmetrically constructed leading and lagging detector arrangement, it is possible in principle to dispense with lossy filtering between the reflected light and fluorescent light in the case of an object in which, because of the assumed symmetrical scatter characteristic of the reflected light, a regular reflection does not occur at irregular structures, so that the efficiency of the arrangement is increased.

Through the use of the symmetrically leading and lagging detector arrangement, it is also possible to detect and eliminate the time-dependent influence of the measurement arrangement.

When using the symmetrically leading and lagging detector arrangement, it is assumed that the fluorescence excitation is carried out with short-wave light, for which the penetration depth is small. Further, because the scanning speed is very low compared with the speed of light, it can be assumed that the partially isotropically scattered or statically fluorescing light components strike the advancing and retreating detector portions simultaneously.

For this reason, the image which leads the confocal detector by time ti is subtracted from every image lagging behind the confocal detector by time ti in a pixel-correlated manner. An image position correction according to the reflection image for compensating for eye movements and an averaging of the fluorescence images which were scanned at the same time ti is advisably carried out on the basis of the differential images.

Figure 3:
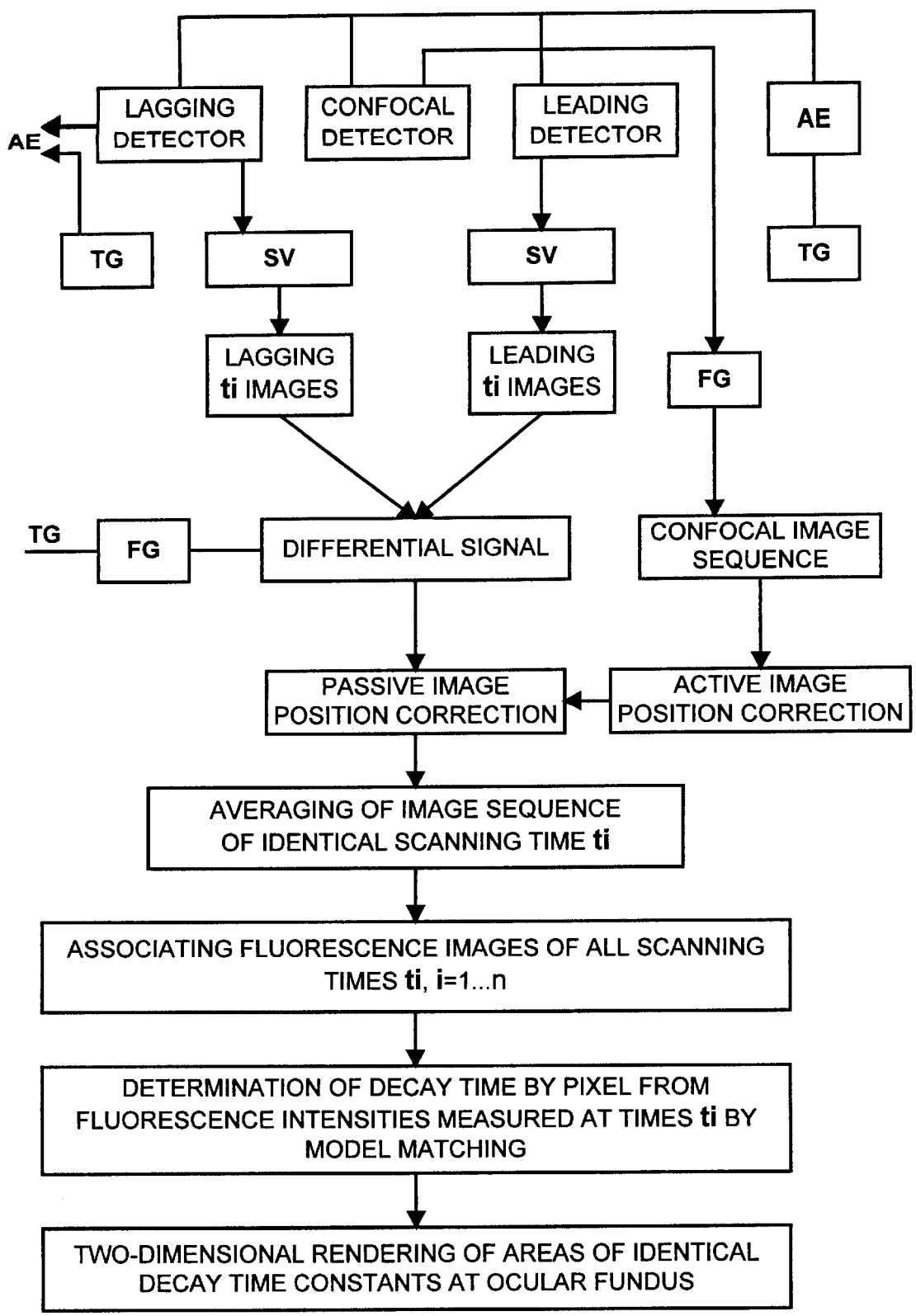
FIG. 3 is a block diagram showing the process steps for obtaining the fluorescence decay time and its two-dimensional rendering on the ocular fundus.

FIG. 3 is a schematic diagram showing the method according to the invention, wherein a control unit AE is connected with the clock generators TG, the frame grabber FG for the confocal detector and the leading and lagging detectors. The confocal detector supplies a sequence of confocal images in the scanning clock.

The outputs of the leading and lagging detectors are connected with signal processing stages SV, where the incoming signals are amplified and linked together.

The serial differential signal is obtained from the difference of the detectors lagging by measurement times ti and the detectors leading by ti' and serves to form a differential image by means of a frame gabber FG for every delay time from which the influence of reflected light, scatter light and static fluorescent light is eliminated.

In order to bring the differential signals of the points on the object into coincidence with the recorded confocal image, an image position correction is carried out through the confocal image sequence and its recorded structures by means of a corresponding transformation rule for every image point, since the differential image sequence has no contours for image matching. As a result, the recorded images lie on top of one another so as to be coincident (active image position correction) or the transformation rule of confocal matching is transferred to the pixels of the differential images (passive image position correction).

In order to improve the signal-to-noise ratio, it is advantageous to average a plurality of differential images of identical scanning times. Due to eye movements, it must be taken into account that no coincident images will be obtained with repeated scanning of the ocular fundus and that nonlinear distortions between the images to be determined must be compensated.

However, as a rule, the fluorescence signals do not exhibit sufficiently contrasting structures suitable as anchor points for the calculation of coefficients of the transformation polynomials for correlating identical image points.

Since the reflection image is obtained from the signal of the confocal detector simultaneously with the fluorescence images, a correction of the differential images of identical scanning times can be carried out proceeding from a spatial correction of the reflection images with the identical correction algorithm.

In the case of active image position correction, identical structures of the ocular fundus from successively recorded reflection images are superimposed. The transformations calculated for each reflection image to be matched are transferred in accordance with pixel to the associated fluorescence differential images in a passive image position correction. A mean image is then calculated for every scanning period ti.

After these operations, there is a sequence of intensity values at time points ti which is associated with every image point, these intensity values forming the support points for the calculation of the fluorescence decay behavior at every image point.

Since the fluorescence decay times are independent from the concentration of the fluorophore, two-dimensional distributions of fluorophores with different decay behavior can be represented in a particularly advantageous manner even if the fluorescent light of different fluorophores lies in the same spectral region or if there are very sharp differences in intensity between the static fluorescence signals.

In addition to its application in ophthalmology, the arrangement according to the invention can also be used to analyze the influence of light at different depths of light-scattering tissues. Light that is reflected in near-surface layers is recorded by detectors that are arranged close to the confocal detector. Light which penetrates deeper into the tissue, on the other hand, has a difference in travel time compared with the light reflected at the surface, wherein this difference is recorded by the lagging detectors which are located at a greater distance from the confocal detector.

In this case, it is necessary that the specimen fluoresces at different layer depths. It is sufficient if the specimen has spatial differences in two-dimensional reflection—absorption—or scatter behavior in layers at different depths.

FIG. 5 shows the described principle for the measurement of light components from different tissue depths.

FIG. 5a shows how the laser beam 2 illuminates the specimen point 7 and the light reflected at the surface is recorded by the confocal detector 8.

In FIG. 5b, the laser beam t1 is moved farther by x1 on the specimen. Light originating from an intermediate layer Z1 is now recorded at the detector 10.

FIG. 5c shows that the laser beam 2, after time t2, illuminates a location at a distance of x2 from the specimen point 7.

The light on the detector element still coming from the specimen comes from an intermediate layer Z2 located at a greater depth than Z1.

While the foregoing description and drawings represent the present invention, it will be obvious to those skilled in the art that various changes may be made therein without departing from the true spirit and scope of the present invention.

What is claimed is :

1. An arrangement for spatially resolved acquisition of an object comprising:

an illumination arrangement for illuminating the object;

means for providing a relative movement between the illumination arrangement and the object by moving the object and/or the illumination arrangement;

at least one confocally arranged detection element for confocal acquisition of the light coming from points on the object; and at least one additional detection element for the acquisition of object light at least posterior in time to the confocal acquisition.

2. The arrangement according to claim 1 for the examination of light-scattering objects, wherein light from different layers of the object is detected and evaluated by the additional detection elements posterior in time to the confocal detection.

3. The arrangement according to claim 2 for the examination of light scattering biological objects.

4. The arrangement according to claim 1, wherein confocal detectors and additional detectors are a component part of a matrix of detectors, wherein parts of the matrix are connected as a detector group for acquisition of time processes or depth-resolved acquisition of the object.

5. The arrangement according to claim 1, with any desired programmed relative movement between the confocal detector and object and control of detector elements, located in the neighborhood of the confocal detector, of a detector matrix for measurement at least posterior in time to the confocal detection.

6. The arrangement for at least two-dimensionally spatially resolved measurement of time processes, especially fluorescence decay times, using a scanning laser ophthalmoscope, wherein the radiation receiver is at least a series of detectors which are arranged in such a way that there is a series of additional detector elements in addition to the confocal detector elements at least subsequently in the scanning direction.

7. The arrangement according to claim 6, wherein the fluorescence decay times are at the ocular fundus.

8. The arrangement according to claim 6, wherein the detectors are arranged in lines and/or in columns.

9. The arrangement according to claim 6, wherein, for the acquisition of the scattered light at special detector elements, the detector line is constructed symmetric to the confocal detector element at least in one scanning direction.

10. The arrangement according to claim 6, wherein the series of detectors for determining short decay times is arranged in the direction of the relative movement between confocal detector and object.

11. The arrangement according to claim 6, wherein the series of detectors for determining longer decay times is arranged vertical to the direction of the relative movement.

12. The arrangement according to claim 6, wherein at least a line of confocal detectors carries out a relative movement with respect to the object and a series of detector elements is assigned to each of the confocal detectors.

13. In a method for the spatially resolved acquisition of an illuminated object comprising the step of carrying out at least a second acquisition of object light at least for individual points on the object at least posterior in time to a first detection of object light for detected identical object points or regions.

14. The method according to claim 13, wherein at least one detection is carried out anterior and posterior in time to a confocal detection.

15. The method for the operation of a confocal scanning laser arrangement according to claim 13, wherein the at least second detection is carried out before the same object point is reached again by the laser beam.

16. A method in accordance with claim 13, further including the step of using the method for the acquisition of fluorescence images.

17. A method in accordance with claim 13, including the step of using the method for the depth-resolved acquisition of object structures, especially of biological tissues.

18. A method for two-dimensionally spatially resolved acquisition of time processes, especially of fluorescence processes and their progress, comprising the the steps of:

scanning the object to be examined by an excitation beam at high speed and, in doing so, in temporal succession exciting every object point to back-reflection;

measuring the light which is reflected back from the object by a plurality of detectors; and using at least one detector element which lags in time with respect to the scanning direction for measuring the back-reflection from this object after time $t=n*xi/v$, where v represents the scanning speed, xi represents $i=0 \ldots n$ spacing of the detector elements;

wherein an image which is delayed in time by ti is formed from the signals of the lagging detector element, so that a series of images is formed corresponding to times ti.

19. The method for two-dimensionally spatially resolved acquisition of time processes, especially of fluorescence processes and their progress, according to claim 18, wherein the measurement of the light reflected back by the object is carried out by a detector arrangement in which an element confocal to the illuminated object site detects the reflected light (regular reflection and central scatter light) and the light of a static fluorescence, a detector element which lags with respect to the scanning direction measures the fluorescence signal of this site after a time $t=n*xi/v$, so that a series of images is available as support points for the calculation of the decay time constant for every object site.

20. The method according to claim 19, wherein the scanning is carried out repeatedly to improve the signal-to-noise ratio.

21. The method according to claim 18, wherein, for the correction of the scattered light component at the lagging detector element xi, which is caused by the excitation light, the light component measured by the leading detector element arranged symmetric thereto is subtracted.

22. The method for position correction of the images associated with different decay times according to claim 18, wherein the radiation image acquired by the confocal detector element is used as a reference image for an image matching.

23. The method according to claim 18, wherein an averaging of the images associated with identical decay times ti is carried out.

* * * * *